United States Patent [19]

Zimmerman

[11] Patent Number: 5,075,506
[45] Date of Patent: Dec. 24, 1991

[54] CONTINUOUS PREPARATION OF SECONDARY AMINES FROM NITRILES USING COBALT AND ZIRCONIUM

[75] Inventor: Robert L. Zimmerman, Austin, Tex.

[73] Assignee: Texaco Chemical Company, White Plains, N.Y.

[21] Appl. No.: 506,747

[22] Filed: Apr. 10, 1990

[51] Int. Cl.$^5$ ............................................. C07C 209/00
[52] U.S. Cl. ...................................... 564/490; 502/325
[58] Field of Search .......................................... 564/490

[56] References Cited

U.S. PATENT DOCUMENTS

| | | | |
|---|---|---|---|
| 1,830,705 | 11/1931 | Marx et al. | 564/490 |
| 2,781,399 | 2/1957 | Shapiro | 564/490 |
| 2,811,556 | 10/1957 | Shapiro | 564/490 |
| 4,721,811 | 1/1988 | Sherwin et al. | 564/491 |
| 4,950,429 | 8/1990 | Vagt et al. | 546/243 |

FOREIGN PATENT DOCUMENTS

| | | |
|---|---|---|
| 0021162 | 1/1981 | European Pat. Off. . |
| 0232097 | 8/1987 | European Pat. Off. . |
| 0384542 | 8/1990 | European Pat. Off. . |
| 0133229 | 12/1978 | German Democratic Rep. . |
| 1180972 | 2/1970 | United Kingdom . |
| 1323351 | 7/1973 | United Kingdom . |

OTHER PUBLICATIONS

Tomidokoro, S. et al., "Preparation of Long-Chain Secondary Amines by Reduction of Nitriles", Chemical Abstracts, 106:175777t, Japan Tokkyo Koho JP 6200,901; 1987, p. 671.

Primary Examiner—Glennon H. Hollrah
Assistant Examiner—Scott C. Rand
Attorney, Agent, or Firm—Jack H. Park; Kenneth R. Priem; David L. Mossman

[57] ABSTRACT

A method for producing secondary amines, particularly fatty secondary amines such as ditallowamine from fatty nitriles, such as tallow nitrile over a cobalt catalyst promoted with zirconium has been discovered. The catalyst may be supported on kieselguhr or other support. The reaction gives high selectivity or secondary amine over the coproduced primary and tertiary amines. The reaction may be conducted continuously in the presence of ammonia and hydrogen. The secondary amine proportion may be increased by a second stage using the same catalyst as the first stage, but in the absence of ammonia.

16 Claims, No Drawings

CONTINUOUS PREPARATION OF SECONDARY AMINES FROM NITRILES USING COBALT AND ZIRCONIUM

FIELD OF THE INVENTION

The invention relates to the production of secondary amines from nitriles, and, in one aspect, more particularly relates to the continuous production of secondary amines from nitriles using a single transition metal catalyst.

BACKGROUND OF THE INVENTION

It has long been known that nitriles can be reduced to give amines. Typically a mixture of primary, secondary and tertiary amines are produced, and a common goal is to devise a process by which the result is a yield high in only one of the possible products; that is, has high selectivity to a particular product. The reaction is understood to proceed in two steps, and often the process is a two step process, often using a different catalyst for the two steps. Frequently, the reaction is run as a batch reaction inasmuch as good selectivities have been difficult to achieve using continuous processes.

Particularly useful products from the reaction are the secondary amines. They have found such widespread uses as textile additives, disinfectants, antistatic agents, and organophilic ammonium bentonites. Especially useful are the unsaturated long-chain aliphatic secondary amines since the quaternary ammonium salts thereof can provide softness and antistaticity to various fabrics and hair, and can also be used as a softener for providing water absorbancy and handling ease to treated fabrics. The secondary amine ditallowamine is useful in the preparation of surfactants, but has never been continuously prepared in high selectivity from tallow nitrile. Tallow nitrile has sixteen to eighteen carbon atoms ($C_{16}$ to $C_{18}$).

Of particular interest is British Patent 1,180,972 (equivalent to Oberrauch, Hans, et al. "Secondary Fatty Amines," *Chemical Abstracts*, 70:11108n, West German Patent 1,280,243, 1969, p. 221) which teaches that aliphatic, saturated and unsaturated secondary fatty amines can be prepared by hydrogenation of the corresponding fatty acid nitrile by passing the nitrile at 140°–200° C. and 30–200 atm. of hydrogen together with water over a solid catalyst consisting of 20% copper, 0.8% chromium and 1% alkali metal with a wide-poured silica gel having a specific area of 250–350 m.$^3$/g as the support. See also British Patent 1,323,351 (equivalent to West German Auslegeschrift 1,941,290) which describes a process for making aliphatic saturated secondary amines from nitriles having 8 to 22 carbon atoms per molecule, where in a first step the starting product is hydrogenated to yield a mixture of saturated amines, and in a second step, this mixture is continuously desaminated (i.e., ammonia is split off) optionally with the addition of hydrogen, where each step is carried out in the presence of a fixed bed hydrogenation catalyst. The first step is conducted at a hydrogen pressure of from 100 to 300 atmospheres gauge and at a temperature in the range of from 100° to 200° C., while the second step is conducted at a pressure from 0 to 50 atmospheres and at a temperature in the range from 120° to 220° C. The catalyst used are a cobalt catalyst in the first step and then a copper catalyst; or alternatively a nickel catalyst in the first reaction and a cobalt catalyst in the second.

Of lesser importance is the following group of publications, which includes U.S. Pat. No. 2,781,399, (equivalent to British Pat. 759,291) that teaches production of secondary aliphatic hydrocarbon amines via a batch reaction using a nickel hydrogenation catalyst. A similar process is described in U.S. Pat. No. 2,811,556, except that a copper oxide/chromium oxide catalyst is used.

Tomidokoro, S., et al., "Preparation of Long-Chain Secondary Amines by Reduction of Nitriles," *Chemical Abstracts*, 106:175777t, Japan Tokkyo Koho JP 62 00,901, 1987, p. 671, teaches the preparation of long-chain secondary amines by the reduction of aliphatic nitriles having 8 to 22 carbon atoms over nickel catalysts at 0–6 kg/cm$^2$ gauge and 200° to 230° C. while removing more than 85% formed $NH_3$. Thus, 250 g. of tallow nitrile was reduced over 0.5 g. Ni catalyst at 200°–300° C. and 5 kg/cm$^2$ while removing 93% formed $NH_3$ to give 240 g. of a mixture of primary (3.1%), secondary (91.1%) and tertiary amine (4.3%) amines.

European patent 0 021 162 B1 teaches the production of alkylamines with 12 to 22 carbon atoms by hydrogenating corresponding fatty nitriles in the presence of a nickel or cobalt catalyst. The hydrogen gas reactant is recirculated after removal of ammonia. The new feature is that throughout the reaction the water content of the circulating gas is adjusted to not above 5 g. per cubic meter, under practically zero-pressure conditions, before recycle. Additionally, a process for selectively preparing an unsaturated long-chain aliphatic secondary amine at a high yield involving reducing an unsaturated aliphatic nitrile having 8 to 22 carbon atoms or a nitrile mixture containing said nitrile with hydrogen in the presence of a nickel hydrogenation catalyst and a carboxylic acid amide at a reaction temperature of 160° to 200° C. according to European Patent Application 0 232 097 A2.

A process for the selective production of aliphatic secondary amines from $C_{8-22}$ primary amines using dehydrogenation/hydrogenation catalysts is briefly mentioned in the English abstract to East German Application 133,229-A. In a first stage, the primary amine is dehydrogenated at normal pressure and at 170° to 260° C., by treatment with a inert gas ($N_2$) in an amount of 5 to 150 l/mol./h., for 30 to 60 minutes until a degree of conversion of the starting material of 85-98% is achieved. The resulting dehydrogenated product is then reacted with hydrogen at 100° to 140° C. and 0 to 50 atmospheres for 10 to 30 minutes to form the secondary amine. The nature of the catalyst was not mentioned in the abstract.

There remains a need for a continuous process for producing fatty secondary amines simply, and in high selectivities. Ideally, such a process would only use one catalyst.

SUMMARY OF THE INVENTION

Accordingly, it is an object of the present invention to provide a process for the continuous production of fatty secondary amines.

It is another object of the present invention to provide a continuous process for making fatty secondary amines that requires only one catalyst.

Another object of the invention is to provide a continuous process for producing fatty secondary amines in high selectivity.

In carrying out these and other objects of the invention, there is provided, in one form, a continuous process for the preparation of secondary amines from nitriles comprising continuously passing a nitrile over a cobalt catalyst promoted with an effective amount of zirconium.

DETAILED DESCRIPTION OF THE INVENTION

It has been discovered that secondary amines, particularly fatty secondary amines such as ditallowamines may be produced in high selectivity by passing the corresponding nitrile, such as tallow nitrile, over a cobalt catalyst promoted with an effective amount of zirconium.

The invention is particularly suited for producing fatty secondary amines from fatty nitriles, which are defined as having from about 8 to about 22 carbon atoms. A preferred feedstock because of its relative inexpensiveness is tallow nitrile which has from about 16 to 18 carbon atoms. Of course, the resulting secondary amine has twice the carbon atoms of the beginning nitrile.

As noted, the catalyst should be a cobalt hydrogenation-dehydrogenation catalyst, such as cobalt oxide. Another suitable cobalt catalyst is cobalt metal, but the process is not limited to these two cobalt materials. Preferably, the promoter is zirconium in a form such as zirconium oxide, for example. In one aspect, the cobalt proportion of the catalyst should range from about 30 to about 70%, preferably from about 40 to about 60%. The promoter, such as zirconium in oxide form, should be present in an amount great enough to give a promotive effect. In one aspect, the amount of promoter may range from about 1 to about 5%, more preferably from about 2 to about 3%.

The catalyst may be supported upon kieselguhr, also known as diatomaceous earth, diatomite and infusorial earth. The catalyst may also be supported on materials including, but not limited to alumina, silica or titania. The reaction may be conducted in two steps. Surprisingly, it was discovered that the same catalyst may be used even if a two-step process is desired. The inventive process also gives a higher secondary amine content than other known continuous processes.

The reaction is preferably conducted at elevated temperatures and pressures. For example, the temperature may range from about 100° to about 200° C., preferably from about 130° to about 180° C. The pressure may range from about 50 to about 5000 psig, and more preferably range from about 200 to about 1000 psig. It is preferred that ammonia and hydrogen are present during the reaction. If the reaction is conducted in two continuous stages, ammonia is preferably not present in the second stage. The absence of ammonia in the second step is preferred since primary amines are formed in the first reaction, and the production of the secondary amines from two primary amines in the second step also produces an ammonia molecule. Thus, the absence of ammonia in the second step would facilitate the second reaction.

The use of a continuous reaction has advantages over the batch reactions in that no filtration or loss of catalyst is experienced, since a fixed bed is used in the continuous reaction. The invention will be illustrated in greater detail with reference to the following examples.

EXAMPLES 1-2

Production of Ditallowamine

Example 1

For the following experiments a tubular reactor filled with 430 cc of catalyst was used. The catalyst used was about 52% cobalt oxide and about 2.5% zirconium oxide on a kieselguhr support. Tallow nitrile was fed at a rate of 0.69 lb/hr., ammonia at 0.12 lb/hr. and hydrogen at 355 l/hr. The reactor pressure was 500 psig and the hot spot temperature was 145° C. As the effluent came out of the reactor, the excess ammonia was allowed to evaporate. This product contained about 36% primary amine, 62% secondary amine and 2% tertiary amine.

Example 2

The product from Example 1 was then run through the reactor again at a rate of 0.75 lb/hr. No ammonia was added to the reactor. The hydrogen feed rate was 355 l/hr. and the pressure was still 500 psig. The temperature was 150° C.

The crude product was stripped under vacuum to remove ammonia. The final product contained about 2% primary amine, 93% secondary amine and 5% tertiary amine. The yield of secondary amine (hydrogenated ditallowamine) is better than 90.3% in example 1 of British Patent 1,323,351, or the 90.5% in example 1 of British Patent 1,180,972.

Such excellent results in the continuous production of ditallow-amine from tallow nitrile using a single catalyst are unknown in the art. Many modifications may be made in the process of this invention without departing from the spirit and scope thereof which are defined only in the appended claims. For example, one skilled in the art may discover that particular reaction conditions or sequences, or catalyst support, which may not be explicitly recited herein, but which are nevertheless anticipated, would give desirable results.

I claim:

1. A continuous process for the preparation of secondary amines from nitriles comprising continuously passing a nitrile over a cobalt catalyst promoted with an effective amount of zirconium at a temperature in the range of about 130° to about 180° C. to give a yield to secondary amine of at least 80%.

2. The process of claim 1 where the catalyst is supported on kieselguhr.

3. The process of claim 1 where the process is carried out in the presence of ammonia and hydrogen.

4. The process of claim 1 where the process is carried out at a pressure in the range of about 50 to about 5000 psig.

5. The process of claim 1 where the catalyst comprises cobalt oxide and zirconium oxide.

6. The process of claim 5 where the catalyst is at least 30% cobalt oxide and at least 1% zirconium oxide.

7. The process of claim 1 where the nitrile has from 8 to 22 carbon atoms.

8. A continuous process for the preparation of secondary amines from nitriles comprising the steps of:
continuously passing a nitrile over a cobalt catalyst promoted with an effective amount of zirconium, in the presence of added ammonia and hydrogen to produce an intermediate reaction product; and continuously passing the intermediate reaction product over the same catalyst in the presence of hydrogen but the absence of ammonia where the process is carried out at a temperature in the range of about 130° to about 180° C. to give a yield to secondary amine of at least 80%.

9. The process of claim 8 where the catalyst is supported on kieselguhr.

10. The process of claim 8 where the process is carried out at a pressure in the range of about 50 to about 5000 psig.

11. The process of claim 8 where the catalyst comprises cobalt oxide and zirconium oxide.

12. The process of claim 11 where the catalyst is at least 30% cobalt oxide and at least 1% zirconium oxide.

13. The process of claim 8 where the nitrile has from 8 to 22 carbon atoms.

14. A continuous process for the preparation of secondary amines from nitriles comprising the steps of:

continuously passing a nitrile having 8 to 22 carbon atoms over a cobalt catalyst supported on kieselguhr promoted with an effective amount of zirconium, in the presence of added ammonia and hydrogen to produce an intermediate reaction product; and continuously passing the intermediate reaction product over the same catalyst in the presence of hydrogen but the absence of ammonia;

where the process is carried out at a temperature in the range of about 130° to about 180° C. and a pressure in the range of about 50 to about 5000 psig. to give a yield to secondary amine of at least 80%.

15. The process of claim 14 where the catalyst is at least 30% cobalt oxide and at least 1% zirconium oxide.

16. The process of claim 14 conducted in the absence of an additional catalyst.

* * * * *